United States Patent
Hajgato et al.

(10) Patent No.: US 9,113,946 B2
(45) Date of Patent: Aug. 25, 2015

(54) BLADE UNIT FOR SURGICAL SCALPEL

(75) Inventors: Julius Hajgato, Ontario (CA); Lee McDonald, Ontario (CA)

(73) Assignee: Southmedic Incorporated, Barrie, Ontario (CA)

( * ) Notice: Subject to any disclaimer, the term of this patent is extended or adjusted under 35 U.S.C. 154(b) by 345 days.

(21) Appl. No.: 13/322,807

(22) PCT Filed: May 12, 2010

(86) PCT No.: PCT/CA2010/000703
§ 371 (c)(1),
(2), (4) Date: Nov. 28, 2011

(87) PCT Pub. No.: WO2010/135812
PCT Pub. Date: Dec. 2, 2010

(65) Prior Publication Data
US 2012/0083816 A1 Apr. 5, 2012

Related U.S. Application Data

(60) Provisional application No. 61/181,018, filed on May 26, 2009.

(51) Int. Cl.
*A61B 17/3213* (2006.01)
*A61B 17/3215* (2006.01)
*A61B 17/3211* (2006.01)
*A61B 19/00* (2006.01)

(52) U.S. Cl.
CPC ......... *A61B 17/3213* (2013.01); *A61B 17/3215* (2013.01); *A61B 2017/32113* (2013.01); *A61B 2019/4805* (2013.01)

(58) Field of Classification Search
CPC ............ A61B 2019/4805; A61B 2017/32116; A61B 2017/32113; A61B 17/3215; A61B 17/3213; A61B 17/3211
USPC ............... 30/2, 151, 156, 162, 164, 286, 285, 30/284, 335; 606/167, 166
See application file for complete search history.

(56) References Cited

U.S. PATENT DOCUMENTS

| | | | | | |
|---|---|---|---|---|---|
| 2,960,769 | A | * | 11/1960 | Matwijcow | 30/340 |
| 3,262,205 | A | * | 7/1966 | Arden | 30/338 |
| 3,311,976 | A | * | 4/1967 | Matwijcow | 30/335 |
| 3,412,467 | A | * | 11/1968 | Matwijcow | 30/335 |
| 3,793,726 | A | * | 2/1974 | Schrank | 30/151 |

(Continued)

FOREIGN PATENT DOCUMENTS

| CA | 2499661 A1 | 4/2004 |
|---|---|---|
| CA | 2563881 A1 | 9/2005 |

(Continued)

*Primary Examiner* — Sean Michalski
*Assistant Examiner* — Jonathan G Riley
(74) *Attorney, Agent, or Firm* — Hovey Williams LLP

(57) ABSTRACT

A scalpel is disclosed, having a conventional handle and a blade unit for releasable attachment to the handle. The blade unit includes a body, a slot within said body to releasably engage the finger protruding from the handle, a scalpel blade attached to said body, and a blade cover slideably engaged to said body and configured for movement between a forward, protective position fully covering said blade and a retracted position to expose said blade for use. The cover has open front and rear ends to permit said blade and said body respectively to protrude through opposing ends of said cover when said cover is moved between said positions.

22 Claims, 13 Drawing Sheets

(56) References Cited

U.S. PATENT DOCUMENTS

| | | | |
|---|---|---|---|
| 4,823,457 A * | 4/1989 | Prochaska | 29/509 |
| 5,088,173 A * | 2/1992 | Kromer et al. | 29/239 |
| 5,342,379 A | 8/1994 | Volinsky | |
| 5,527,329 A * | 6/1996 | Gharibian | 606/167 |
| 5,571,132 A * | 11/1996 | Mawhirt et al. | 606/182 |
| 5,827,309 A * | 10/1998 | Jolly et al. | 606/167 |
| 5,868,771 A * | 2/1999 | Herbert et al. | 606/167 |
| 5,938,027 A * | 8/1999 | Soroff et al. | 206/370 |
| 5,938,676 A * | 8/1999 | Cohn et al. | 606/167 |
| 5,941,892 A * | 8/1999 | Cohn et al. | 606/167 |
| 6,053,929 A * | 4/2000 | Cohn et al. | 606/167 |
| 6,457,575 B2 * | 10/2002 | Swinderman | 198/499 |
| 6,500,187 B1 * | 12/2002 | Petersen | 606/167 |
| 6,629,985 B1 * | 10/2003 | Kiehne | 606/167 |
| 7,207,999 B2 * | 4/2007 | Griffin et al. | 606/167 |
| 8,074,364 B2 * | 12/2011 | Nakamura | 30/335 |
| 8,567,072 B2 * | 10/2013 | Yi et al. | 30/162 |
| 2004/0098004 A1 * | 5/2004 | George et al. | 606/167 |
| 2005/0203555 A1 | 9/2005 | Griffin et al. | |
| 2006/0095057 A1 * | 5/2006 | Yi et al. | 606/167 |
| 2006/0212058 A1 | 9/2006 | Djordjevic et al. | 606/167 |
| 2006/0241664 A1 * | 10/2006 | Lam | 606/167 |
| 2007/0156160 A1 * | 7/2007 | Petersen | 606/167 |
| 2007/0255298 A1 * | 11/2007 | Djordjevic et al. | 606/167 |
| 2007/0265651 A1 * | 11/2007 | Yi et al. | 606/167 |
| 2013/0079804 A1 * | 3/2013 | Milton et al. | 606/167 |
| 2013/0331871 A1 * | 12/2013 | Milton et al. | 606/167 |

FOREIGN PATENT DOCUMENTS

| | | |
|---|---|---|
| EP | 0988832 | 3/2000 |
| EP | 0988832 A2 | 3/2000 |
| JP | H11318913 | 11/1999 |
| JP | 2005538781 | 12/2005 |
| WO | 2004026151 | 4/2004 |
| WO | 2010135812 A9 | 12/2010 |
| WO | PCT/CA2010/00073 | 12/2010 |

* cited by examiner

BLADE UNIT FOR SURGICAL SCALPEL

RELATED APPLICATION

This is a National Phase Application pursuant to 35 U.S.C. §371 of International Application No. PCT/CA2010/000703, filed May 12, 2010, which claims priority from U.S. Provisional Patent Application No. 61/181,018, filed May 26, 2009, both of which are hereby incorporated by reference in their entireties.

RELATED APPLICATION

This application claims the benefit of U.S. Provisional Application No. 61/181,018 filed on May 26, 2009, which is herein incorporated by reference.

FIELD OF THE INVENTION

The invention relates to scalpels for surgery and other procedures, in particular a scalpel with a blade cover to protect the blade and to protect against injury from an unprotected blade. The blade cover may comprise a removable blade unit that can be mounted to a conventional scalpel handle. The invention further relates to a kit consisting of a scalpel handle and a removable blade unit.

BACKGROUND OF THE INVENTION

The scalpel is a basic tool for surgeons. Scalpels are generally available in either a fully disposable or a re-usable form. The most common form of reusable (non-disposable) scalpel includes an elongate metal handle, with a blade mount projecting from an end of the handle. The conventional type of blade mount consists of a finger projecting from an end of the handle, with longitudinal grooves disposed on opposing sides thereof to receive a slotted opening in a blade. A disposable blade (referred to as a "sharp") is provided, usually in a foil package, which includes a slot configured to lock onto the finger. Opposing sides of the slot are received within the grooves to retain the blade to the handle. In order to mount the blade, the user must carefully remove the blade from its packaging and clip the blade onto the finger. In order to protect the user from contact with the blade during this procedure, the blade can be handled with forceps or other handling tool. Care must be taken to avoid dropping the blade, since even if the blade strikes a sterile tray or bowl and could in principle be used, the blade can be dulled. Removal of the blade after use also presents particular risks, since at this point the blade is contaminated. This step requires the user to manipulate the blade, which presents a risk of injury with potentially serious consequences to the user's health and safety. As well, careful and deliberate manipulation of the blade takes up valuable time in the operating theater.

Replacement of the blade is required with each new surgical procedure, and in some cases the blade may be replaced during the procedure itself, if it has become dulled.

In order to reduce the risk of injury, various means have been proposed to provide a temporary cover for the blade. In some cases, the cover consists of a sheath that slips over the blade during installation and removal of the blade, and which may be removed when the blade is to be used. However, the act of removing or installing the cover itself presents risks. Other proposed solutions have involved a scalpel with a retractable blade. For example, U.S. Pat. No. 7,101,382 to George et al. discloses a retractable scalpel device with two releasable latching elements. When the scalpel blade is in an extended position, each releasable latching element is accessible for depression by finger pressure to cause retraction of the extended blade.

Another device is disclosed in U.S. Pat. No. 5,827,309 to Jolly et al., relating to a surgical scalpel having a movable blade guard that can be retracted to expose the blade and that can be extended to cover the sharp cutting edge of the blade. The guard is mounted inside the blade handle.

Systems that include a retractable guard as disclosed above generally require a specialized handle that is specially configured and adapted for use with the blade guard. In general, such systems are not adapted for use with conventional, commonly-available scalpel handles. This tends to add to the cost of such systems and requires hospitals to stock multiple handle types. More importantly, it can be difficult to overcome the reluctance of surgeons to use a new type of handle with which they are unfamiliar. There is thus a need to provide a system for protecting a blade which avoids drawbacks of conventional removable blade covers, and which is adapted for use with a conventional scalpel handle. Such a system thereby provides an increased level of comfort and familiarity to the surgeon, and permits hospitals to continue to use their supply of existing scalpel handles.

SUMMARY OF THE INVENTION

An object of the present invention is to provide an improved scalpel having a detachable blade unit, wherein the blade unit includes a retractable cover that protects the blade during storage, installation and disposal. A further object is to provide a blade unit for mounting to a scalpel handle, wherein the blade unit includes a body which can be mounted to a scalpel handle prior to use. A scalpel blade and a blade cover are mounted to the body, wherein the cover can slide relative to the body to selectively cover or expose the blade. A further object is to provide an improved blade cover that may be adapted to a variety of scalpels.

One aspect of the invention relates to a blade unit for attachment to a scalpel handle of the type that includes a blade mount comprising an elongate finger which projects forwardly from an end of the handle. Preferably, the scalpel handle is of conventional design, known per se to the art, of the non-disposable variety. The blade unit comprises a body having a mount configured to releasably engage the finger, a scalpel blade attached to said body and protruding forwardly therefrom, and a blade cover slideably engaged to said body. The cover is configured to be moved between a forward, protective position fully covering said blade, and a retracted position wherein said blade is exposed for use and said cover at least partially covers said body. In a third position, the cover may be further extended into a locked position for disposal.

According to another aspect, the body and sliding cover are engaged to each other by at least one mutually cooperating and engaging longitudinal groove and projection which slides within the groove. Preferably, the body comprises a pair of such grooves on opposing sides of the body, and the cover comprises multiple projections configured to fit within the groove to permits the cover the slide longitudinally relative to the body. One or more projections or openings associated with the groove or grooves selectively retain the projections to selectively retain the cover in the multiple retention positions of the cover.

The blade unit may be configured to selectively retain said cover in three positions, comprising a "pre-use" position wherein the cover is not fully extended, but still covers the blade for safe handling, storage, etc., a "retracted" position wherein the cover is retracted rearwardly to expose said blade for use, and a "disposal" position wherein the cover is fully extended and extends past the "pre-use" position for removal of the blade unit from said handle and safe disposal. Preferably, the unit retains said cover in said pre-use and use positions in a releasable fashion, but in the disposal position in a substantially non-releasable fashion. The retention in the "use" position may be achieved by frictional engagement between the cover and body, which permits a degree of longitudinal adjustment to suit the preferences of the user.

The blade unit may be provided as a disposable unit, intended for one-time use. The blade unit may be supplied in a sterile package, or alternatively in loose form for autoclaving or other form of sterilizing prior to use. An advantage of the present invention is that the blade unit is safe for handling when it is in its pre-use configuration with the cover extended over the blade, and does not have to be supplied in an individual foil package, thereby saving on costs as well as eliminating waste and the step of opening and disposing of the foil package.

The blade unit can accommodate various types and sizes of blades, such as industry standard blade. These include, for example, blade nos. #11, #12, #22. The blade unit can also fit the ISO Standard Fitting features of surgical scalpels, such as the ISO small fitting feature (No. 3) and large fitting feature (No. 4), and is adaptable to accept other fitting features as these become available. Alternatively, according to another aspect, the handle may have a non-standard blade mount, with the blade unit being configured to attach to the non-standard mount. For example, for certain applications it may be desirable to provide a unique mounting configuration of the handle and blade unit.

According to another aspect, the invention relates to the combination of a scalpel handle and the blade unit as described above, supplied as a kit. The scalpel and blade unit may be configured for medical/surgical use, or any other use where a scalpel-type cutting implement may be usefully employed, such as for home hobbyists.

According to a further aspect, the invention relates to a method of attaching a blade to a scalpel handle, by providing a blade unit as described above and a scalpel handle having a conventional blade mount, and engaging the blade unit to the handle. Following use, the cover is extended to cover the blade and locked in the covered position, following which the blade unit is removed from the handle for safe disposal.

According to a still further aspect, the invention relates to a scalpel having a blade cover, in which the scalpel includes a body portion to which the blade is attached, and a blade cover slideably engaged to said body and configured for movement between a forward, protective position fully covering said blade and a retracted position to expose said blade for use. The body is configured to selectively retain said cover in three positions comprising a "pre-use" position wherein said cover fully covers said blade for safe handling, a "retracted" position wherein the cover is retracted rearwardly to expose said blade for use, and a "disposal" position wherein said cover is located forwardly past the "pre-use" position for removal of the blade unit from said handle for safe disposal.

The invention will now be further described by a description of non-limiting detailed embodiments. It will be understood that the particular elements, means, components, and the like described herein are presented merely by way of example, and may be varied by persons skilled in the art while remaining within the scope of the invention. As well, any directional references used herein are merely for convenience of description, and do not limit the scope of the invention, which of course may be used in any orientation.

All prior art cited herein is incorporated into this application in its entirety, if and to the extent permitted. References herein to prior art are not intended as an admission in any form that such references constitute prior art for purposes of determining the validity of any of the claims of this application, nor that such art is material to the patentability of the invention.

DETAILED DESCRIPTION OF THE DRAWINGS

Figure 1:
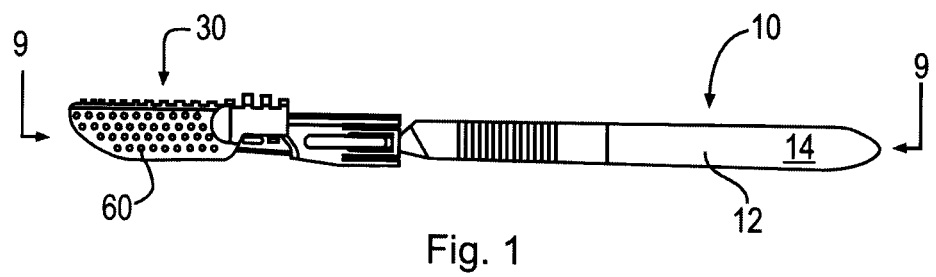
FIG. 1 is a side elevational view of a scalpel with a blade unit according to the present invention, in the closed (protected) position.
Figure 2:
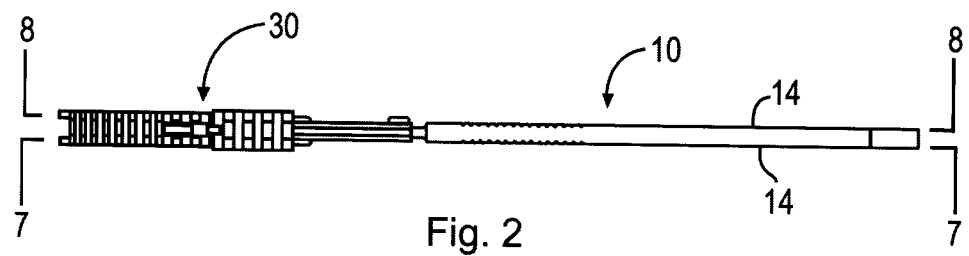
FIG. 2 is a top plan view of the scalpel of FIG. 1.

The embodiment of the scalpel blade unit described herein comprises a conventional scalpel handle 10, such as a Finger™ or Spectrum™ handle. Handle 10 comprises an elongate hand grip portion 12 having flat lateral sides 14 for gripping by the user's fingers. A mounting finger 16 (see FIG. 4) projects forwardly from the handle, configured to mount a blade having a conventional mounting slot. Finger 16 comprises opposing sides, one of which, 16a, is substantially flat, and the other of which, 16b, is inwardly stepped at its proximal end where finger 16 merges with grip portion 10. The inwardly stepped portion is defined by a shoulder 18, which normally assists in the retention of a blade or, in this case, the blade unit, to the handle. Finger 16 includes a pair of opposed grooves 22 recessed into the upper and lower faces of the finger, and extending partway along the length of finger 16. Grooves 22 provide additional means to retain a blade or the like to the handle, as will be described below. Finger 16 is configured to engage a conventional surgical blade, not shown. A conventional blade of this type includes a slot configured to engage the blade to finger 16. The slot comprises a relatively wide proximal segment, into which finger 16 is inserted at an angle, and a narrow distal segment which engages the grooves 22 of finger 16 so as to firmly retain the blade to the handle. The respective configurations of a conventional finger and blade slot meet recognized international standards for compatibility. Handle 10 further comprises a pair of opposed sloping shoulders 19 where the fingers join with the body portion of handle 10. Handle 10 is usually provided with ridges or other tactile features to improve the user's grip.

A separate disposable blade unit 30 is provided, which is releasably attachable to handle 10. FIGS. 4-9 show a first embodiment of blade unit 30, and FIGS. 12-19 show alternative embodiments of blade unit 30. Blade unit 30 may be fabricated by molding of a rigid plastic such as polycarbonate or polyester, which is capable of withstanding hospital autoclaving and other various sterilization methods (such as radiation, ionization, ETO). Body 24 is radio-opaque to aid in localization in the event it is left behind post-operatively within the patient's body.

Blade unit 30 includes a body 24 and a sliding cover 60. Body 24 comprises an elongate generally flat structure, configured for mounting at its proximal end to handle 10. Body 24 includes a mount to releasably mount body 24 to handle 10. The mount comprises a metal plate 25 which is molded, glued or otherwise incorporated into body 24. At least one and preferably both sides of plate 25 are exposed via a recess 32 within body 24, which permits access to the sides of plate 25. Plate 25 includes a slot 27, which is exposed via recess 32. The configuration of slot 27 matches that of the mounting slot of a conventional surgical blade, thereby permitting body 24 to mount to finger 16 in the same manner as a conventional surgical blade. Slot 27 comprises a relatively wide entry segment 34 at its proximal end which is configured to receive finger 16, and a narrower retention segment 36 at the distal end which is inwardly stepped from entry segment 34. Retention segment 36 engages grooves 22 within finger 16 to firmly engage handle 10 to body 24. Preferably, plate 27 is essentially the same in structure as the retention portion of a conventional surgical blade, absent the edge-bearing portion.

Body 24 includes laterally opposed axial grooves 41 adjacent to the upper surface 43 of body 24, configured to slideably engage blade cover 60, as will be described below. The upper surface 43 is generally flat to accommodate cover 60 sliding over body 24.

Figure 7:
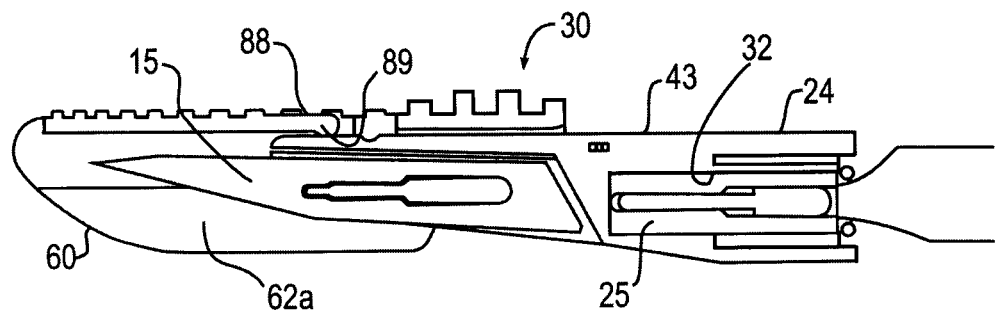
FIG. 7 is a cross-sectional view of the device, along line 7-7 of FIG. 2.
Figure 8:
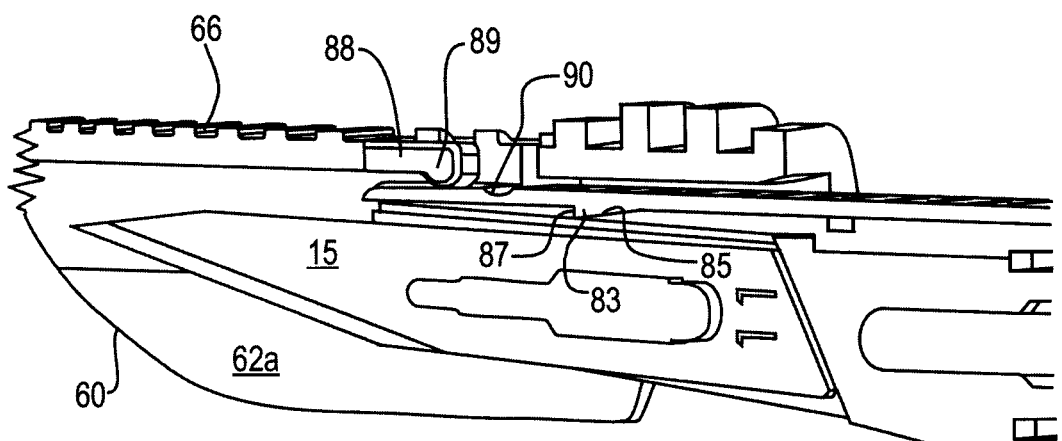
FIG. 8 is a cross-sectional view along line 8-8 of FIG. 2.
Figure 9:
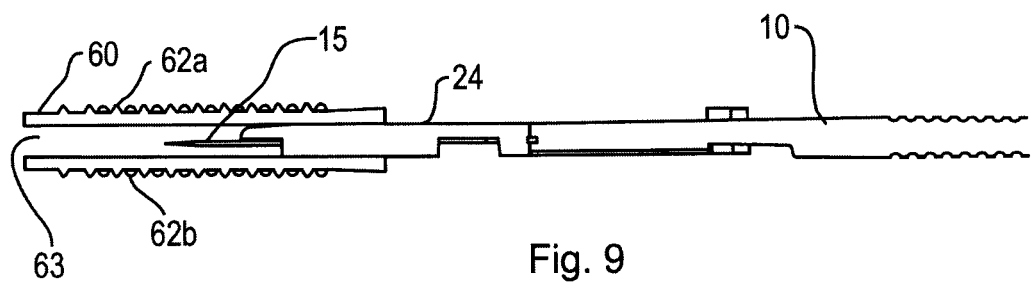
FIG. 9 is a cross-sectional view along line 9-9 of FIG. 1.
Figure 14:
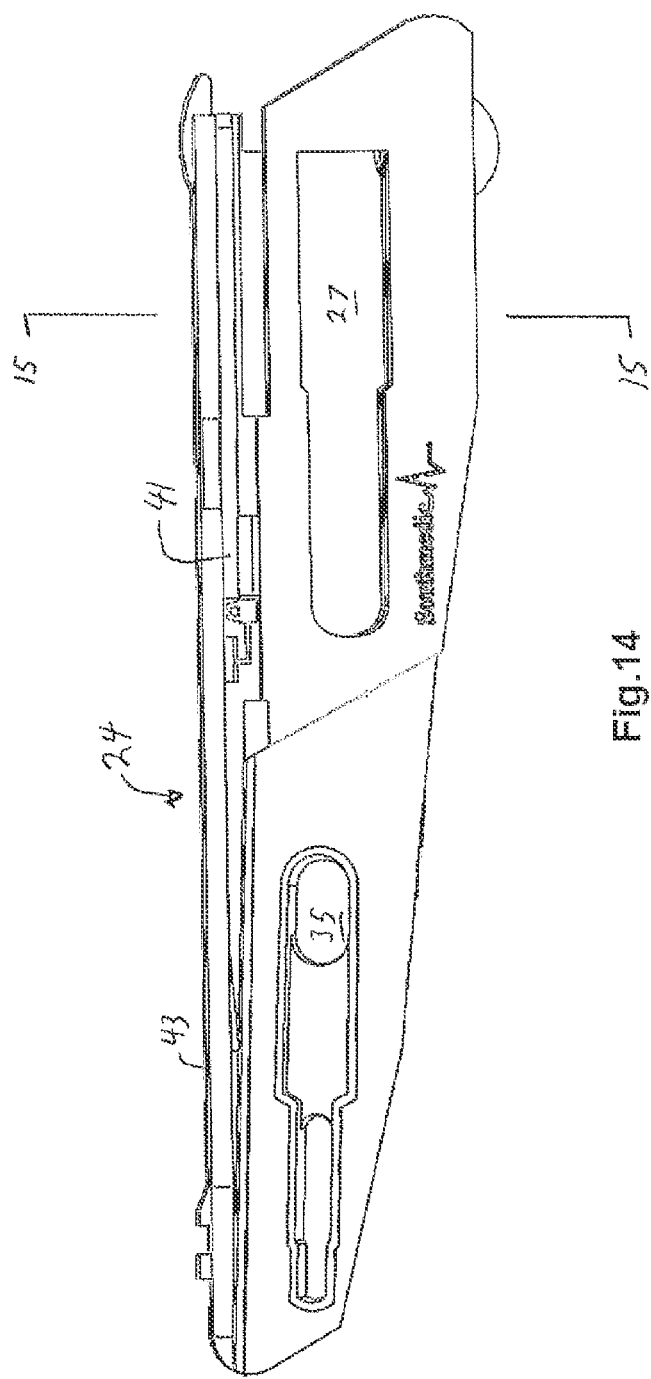
FIG. 14 is a side elevational view of the body portion of the second embodiment.
Figure 15:
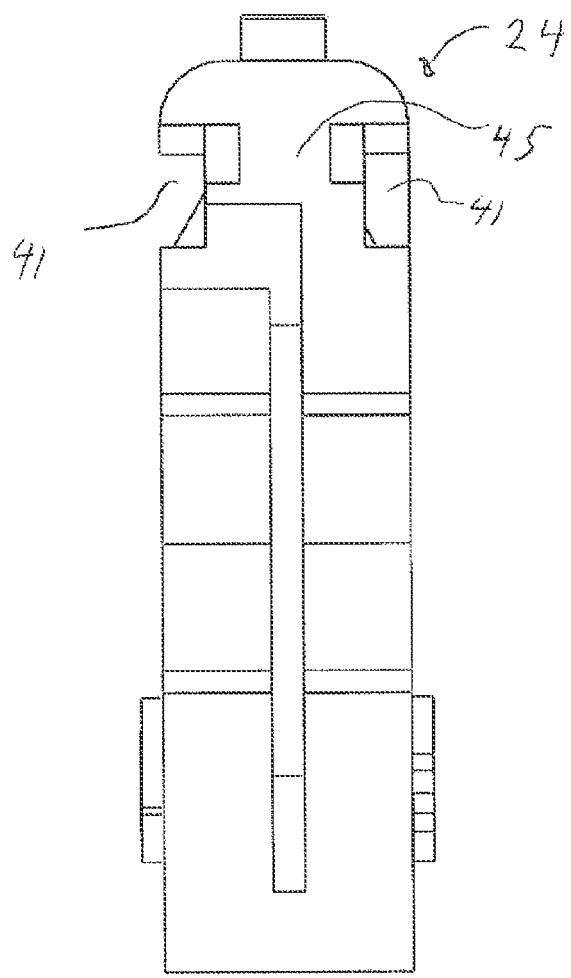
FIG. 15 is a cross-sectional view along line 15-15 of FIG. 14.

As seen in FIGS. 7-9, surgical blade 15 is mounted to body 24. Blade 15 can be permanently fixed to body 24 by melt-fastening or other permanent fastening means and protrudes forwardly therefrom. Alternatively, as seen in FIG. 14, blade 15 can be fastened by mechanical fastening means, such as one or more bosses 35 projecting from body 24 which engage or can be fused to a mounting slot in a surgical blade 15 in a permanent fashion. Blade 15 can comprise a wide range of blade configurations, depending on the desired use, including a conventional surgical blade or alternatively a specially configured blade. Depending on the size and configuration of the selected blade, the overall configuration of the blade unit can be scaled up or down, or otherwise adapted to accommodate the configuration of the selected blade. Persons skilled in the art would readily understand how to make such modifications to the configuration and size of the disclosed blade unit.

Figure 6:
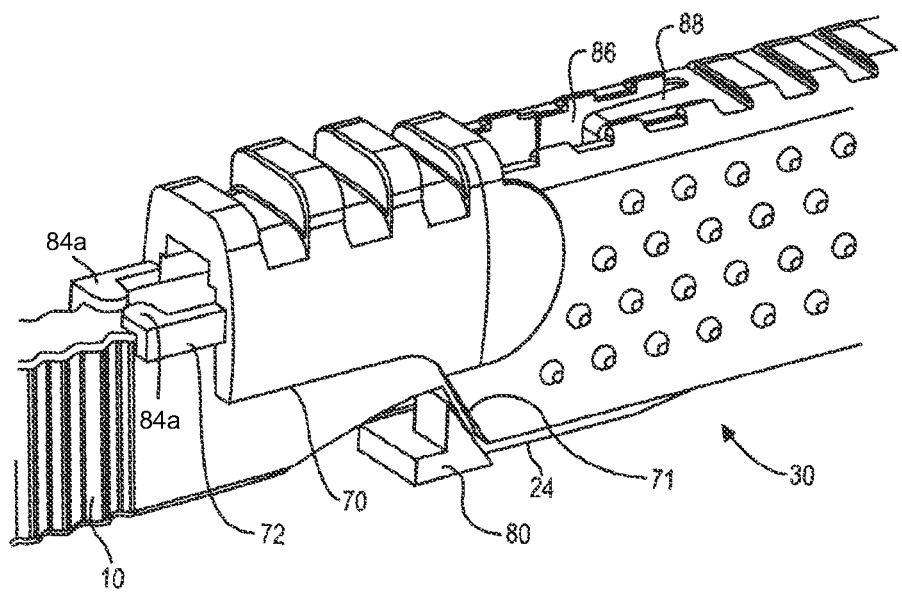
FIG. 6 is a detailed view, in perspective, of a portion of the handle and blade unit in the open position.
Figure 16:
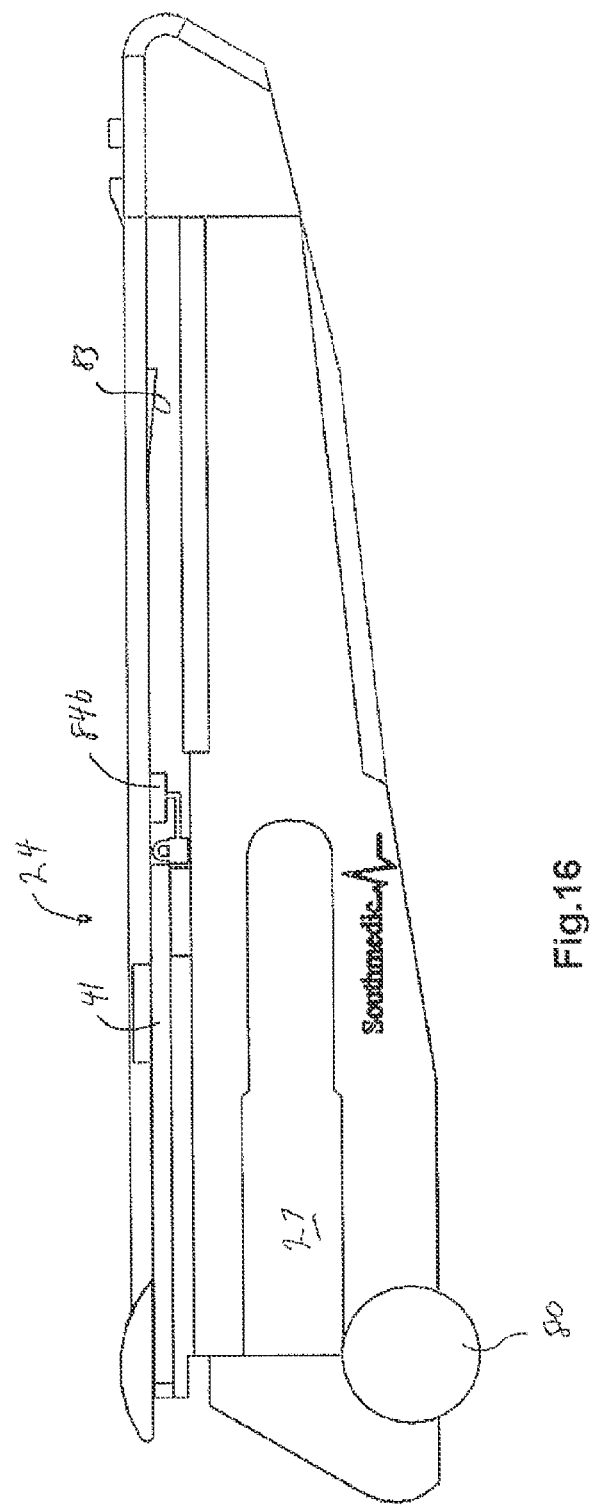
FIG. 16 is a side elevational view of the cover portion of the second embodiment.

As seen in FIG. 6, body 24 includes a stopper 80 protruding laterally from one side thereof, near the proximal end adjacent to the lower edge of body 24. Stopper 80 is configured to contact a face of the blade cover 60, as will be described below. Stopper 80 also serves the function of facilitating release of blade unit 30 from handle 10, by permitting the user to press against stopper 80 to angle handle 10 out of alignment with plate 25, to permit the handle to be withdrawn from slot 27. An alternative configuration of stopper 80 is shown in FIG. 16, wherein stopper 80 is cylindrical.

In order to mount body 24 to handle 10, finger 16 is inserted into and engaged within slot 27, in essentially the same manner as a conventional blade is attached to a handle. Finger 16 is engaged with slot 27 through the laterally-opening recess 32, such that the blade unit and handle are firmly fastened together.

It will be seen that with modifications, body 24 may be configured to mount to a scalpel handle having a different type of mount than the system described above. It is foreseen that different mounting systems may by employed in the art of scalpels and other cutting implements, and in most such cases it would require only a routine modification by a person skilled in the art to adapt the invention to mount to such a handle.

Blade unit 30 includes blade cover 60, which is attached to and slides axially along body 24. Blade cover 60 is composed of spaced apart sidewalls 62a and 62b, the outside surfaces of which include small protrusions or other features to engage the user's grip. The protrusions may be rubberized if desired. Sidewalls 62 are open to below and define a channel 63 therebetween. Blade cover 60 includes a rounded tip 64 which is open to the front, and a knurled upper surface 66. Cover 60 is configured to shield blade 15 when extended relative to body 24; it will be seen that the configuration of cover 60 may vary depending on the size and configuration of blade 15 in order to fully shield blade 15. In the first embodiment described herein, blade 15 is a conventional single-edged triangular scalpel blade. Cover 60 slides axially along body 24. Blade cover 60 is configured to slide along body 24. When blade 15 is covered in either its "pre-use" or "disposal" positions, discussed below, it is recessed within tip 64 by at least several millimeters, to protect the blade tip and prevent any risk of harm to the user.

Sidewalls 62 of cover 60 include a cut-away region 70 at the proximal end thereof, defined by shoulders 71 and configured to expose slot 27 of plate 25 when the cover 60 is retracted to the "use" position wherein the blade is exposed.

Cover 60 is moveable relative to body 24 between three positions defined by the cover being selectively retained in such positions. The initial retention position is a "pre-use" position, which constitutes the position in which the unit is transported, stored and supplied to the user. In this position, cover 60 is substantially (but not fully) extended, so as to fully cover blade 15. The apparatus is supplied to the user with the cover retained in this position in such a fashion that it can be retracted with a moderate but deliberate force to expose the blade, wherein during normal usage an inadvertent retractive force will not dislodge the cover from the position. As discussed below, a detachable guard may cover the front to the blade unit when in this position to further protect the user and prevent contamination of the blade. Blade unit 30 is safe for handling in this position, and may be manipulated by hand to fasten the apparatus to conventional scalpel handle 10.

Figure 3:
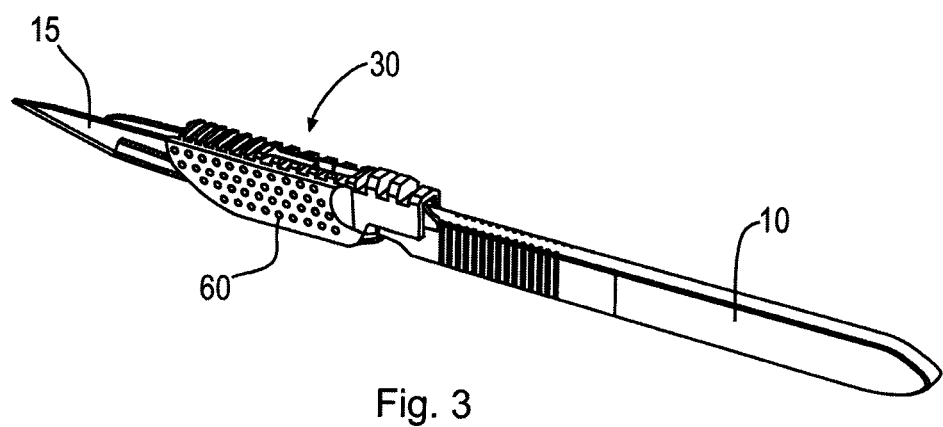
FIG. 3 is a perspective view of the scalpel, with the blade unit in the retracted, open position to expose the blade for use.

The second position is a "retracted" or "use" position, in which the cover is retracted rearwardly to expose blade 15 for use. The cover is held in this position largely by frictional engagement between the cover and body 24. Alternatively or in addition, a non-frictional retention means may be provided, such as a cooperating protrusion and detent arrangement provided in the respective components to provide a "click-stop" retention. In this second position, the surgeon may use the blade in a conventional fashion. When cover 60 is retracted in the "use" position, blade 15 protrudes through open end 62 of cover 60 and is exposed for use by a surgeon, as seen in FIG. 3. Rearward travel of cover 60 is limited by contact between shoulder 71 of cover 60 and stopper 80 to prevent over-retraction of cover 60. Cover 60 is retained in this position by frictional engagement between the inside surfaces of sidewalls 62a and b and the exterior surfaces of body 24.

The third position of the cover is a "disposal" position. In this position, the cover is pulled forwardly past the "pre-use" position, into a fully extended position. When moved into this position, cover 60 fully covers blade 15 and more or less permanently locks into this position. This permits safe removal of the blade holder 30 from handle 10, for disposal in a safe manner. Securely locking the cover into the disposal position results in the device being safe so as to minimize the risk of injury from the used "sharp", and to permit the used device to be disposed of in ordinary hospital (contaminated) garbage, depending on hospital protocols and safety requirements.

Figure 4:
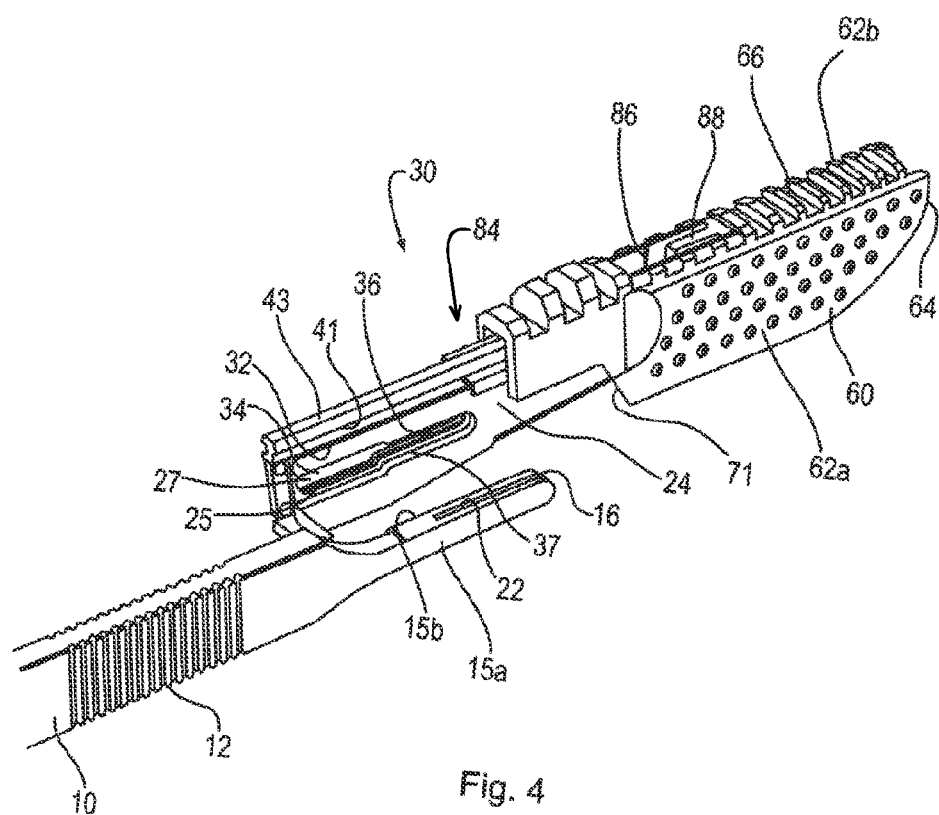
FIG. 4 is a detailed view, in perspective, of a portion of the scalpel handle and blade unit, showing the blade holder detached from the handle.
Figure 5:
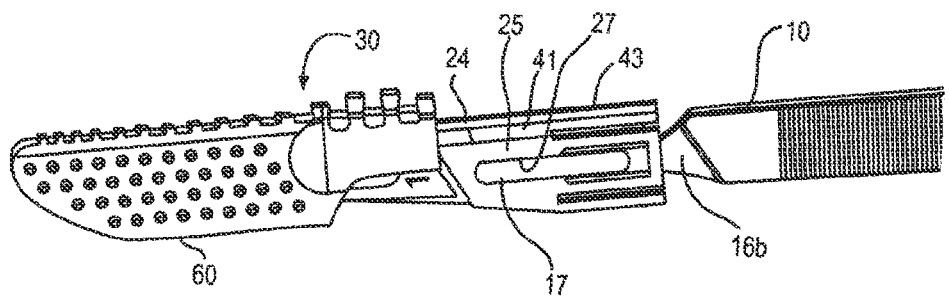
FIG. 5 is a side elevational view of the handle and blade unit in the closed position.
Figure 13:
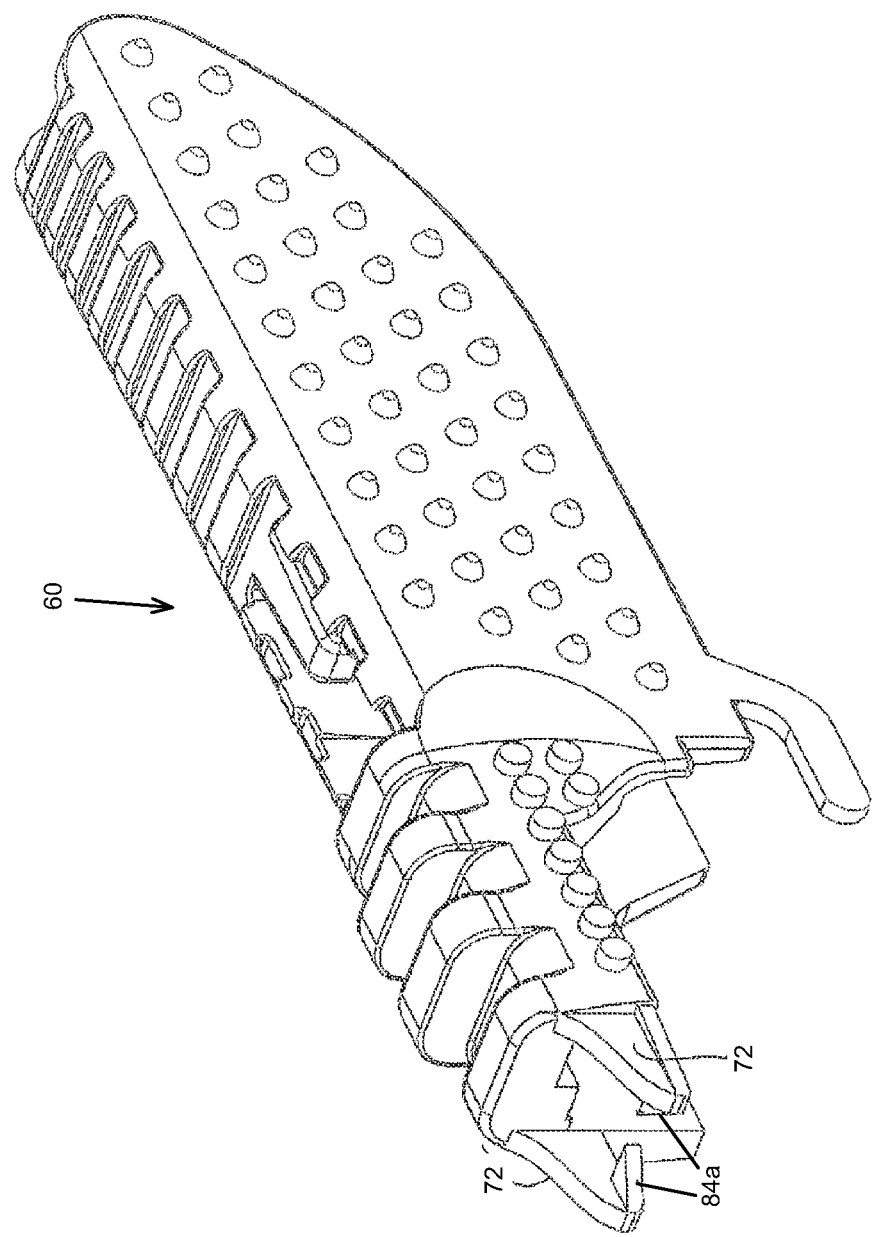
FIG. 13 is a perspective view of a third embodiment, showing a portion of the cover.

In order to slideably retain cover 60 to body 24, two pairs of proximal and distal protrusions 84a and 84b respectively are provided on cover 60. Each pair of protrusions 84a and b consist of individual opposed members which extend inwardly towards each other from the side walls of cover 60. Proximal protrusions 84a, seen in FIG. 6, are located at the end of arms 72 that extend rearwardly from the rear face of cover 60. Arms 72 may be generally elongate, as seen in FIGS. 4 and 6, or alternatively may be generally triangular in profile, as seen in FIG. 13 so as to provide additional support. Protrusions 84b, one of which is shown in FIG. 16, extend inwardly from the inside faces of sidewalls 62a and b of cover 60. Protrusions 84a and b are generally rectangular in profile, and are configured and located to slide within opposing laterally facing channels 41, thereby retaining cover 60 to body 24 while permitting cover 60 to slide axially along body 24 in a fore or aft direction.

Opposing channels 41 are recessed into the upper portion of body 24, parallel to upper surface 43, as seen in FIGS. 4, 5, and 14-17. Channels 41, one of which is shown in detail in FIG. 17, extend lengthwise within body 24 and divided by a central wall 45. Channels 41 are configured to receive opposed sets of protrusions 84, which are oriented laterally inwardly to engage outwardly-facing channels 41. Channels 41 terminate at their distal end in an end wall 43 (see FIG. 17) which serves as a stop to limit the travel of cover 60 past the maximally-extended "disposal" position.

One or more structures are associated with channels 41 for cooperative engagement with protrusions 84a and b, so as selectively retain cover 60 within one or more of its predetermined "stop" locations along body 24. A first such structure is a wedge-shaped member 83 (see FIGS. 8 and 17) extending from one of the walls of channel 41 into the interior of the channel. Member 83 comprises a sloping proximal face 85 which permits urges protrusion 84 downwardly as it traverses over face 85, and a vertical distal face 87 which engages protrusions 84 to prevent retraction of cover 60 once the protrusion has overridden member 83 and is lodged behind it. Member 83 may be provided within one or both of channels 41 on opposing sides of body 24. A further structure comprises one or more horizontal openings 91 within channel 41 recessed into or passing through central wall 45. Opening 91 is configured such that protrusions 84a enter into this recess from opposing sides as these protrusions travel lengthwise within channel 41. Once within the opening, protrusions 84a are prevented from exiting by the abutting vertical walls of the respective opening 91 and protrusions 84a, thereby retaining cover 60 in position. The selected configuration and depth of the respective opening 91 an protrusions 84a will determine the degree of force required to dislodge the protrusions from these openings. Walls 82a and b are resiliently biased to urge protrusions 84 inwardly together, thereby urging protrusions 84 into recess 91. One or more such recesses 91 may be provided, and located to engage one or both sets of protrusions 84a and 84b within any of the selected use, pre-use or disposal positions.

A further retention means is provided to retain cover 60 in the "pre-use" position. In the first embodiment see FIGS. 6-8), cover 60 includes an opening 86 within its upper surface 66. A flexible tab 88 extends partially across opening 86. One end of tab 88 is fixed to upper surface 66, while the other end is unattached to permit the tab 88 to flex. The free end of tab 88 includes a downwardly-facing knob 89 configured to engage a detent 90 within the upper surface 43 of body 24. Recess 90 is positioned such that when tab 88 is engaged within detent 90, cover 60 is held in its pre-use position. This ensures that the blade unit 30 can be handled safely, in particular while blade unit is fitted onto handle 10. In order to release tab 88, when it is desired to safely retract cover 60, cover 60 is retracted with a firm rearward pull, thereby releasing knob 89 from detent 90. Detent 90 and knob 89 are configured with a sufficiently deep profile to require a firm and deliberate movement of cover 60, in cooperation with tab 88 being sufficiently stiff to prevent inadvertent dislodging.

Figure 12:
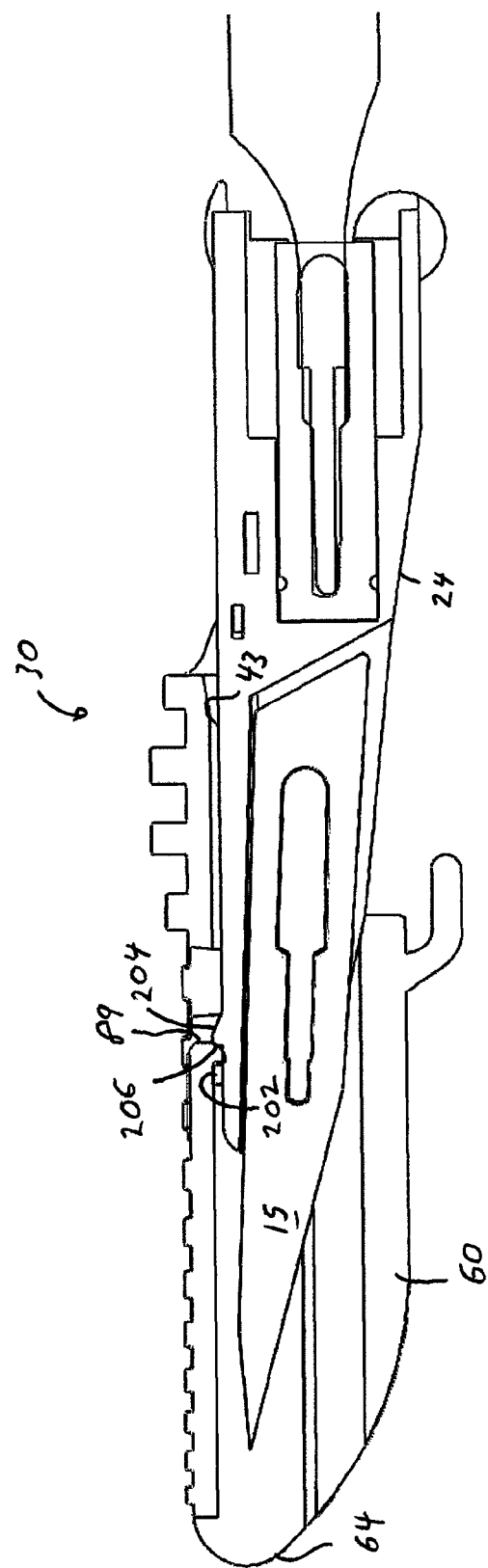
FIG. 12 is a side elevational view of a portion of the blade unit with a portion of the outer structure removed to show internal structure, of a second embodiment thereof.
Figure 17:
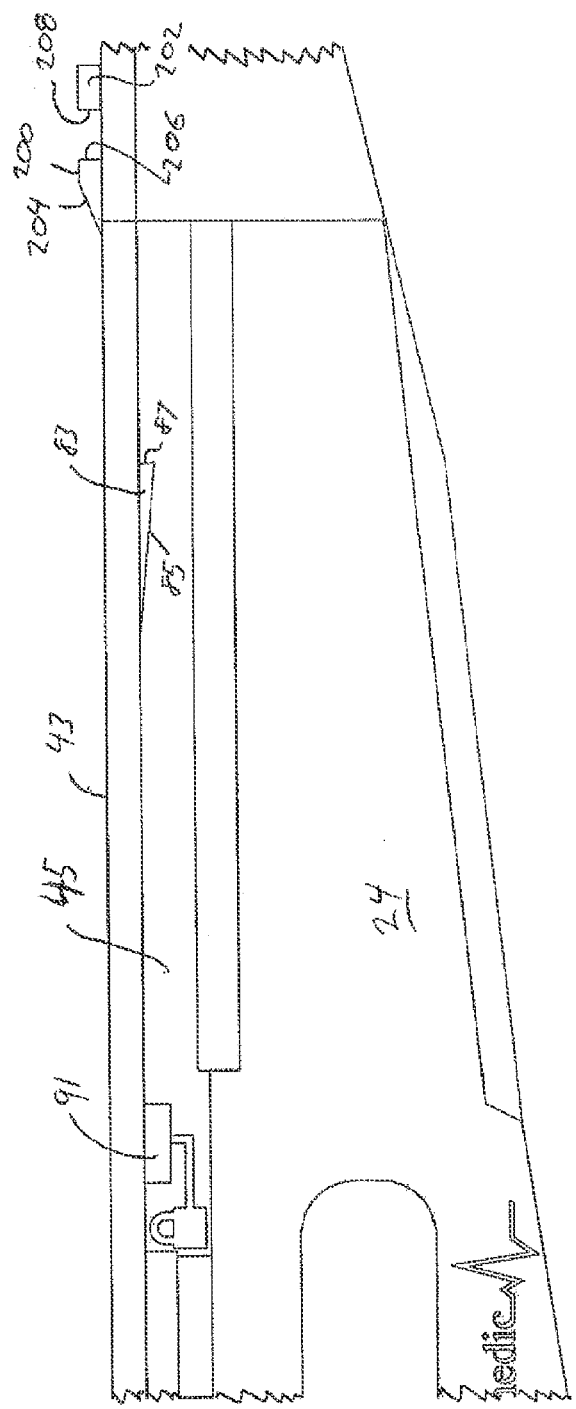
FIG. 17 is a side elevational view of an enlarged portion of the body of the second embodiment.

In order to lock cover 60 into the disposal position following use of the scalpel, a retention means is provided, which may comprise any suitable solution to securely hold the cover in the disposal position. One such means is shown in FIGS. 12 and 17. According to this aspect, a pair of fins protrudes upwardly from upper surface 43 of body 24, comprising proximal fin 200 and distal fin 202 which are spaced apart longitudinally to provide a gap therebetween. Proximal fin 200 is wedge-shaped, comprising a sloping proximal face 204 and a vertical distal face 206. Distal fin 202 has a vertical face 204 facing the gap, such that the gap between fins 200 and 202 is defined by spaced apart vertical faces 206 and 208. Cover 60 is provided with knob 89, which in this embodiment comprises a rounded proximal face and a vertical distal face (FIG. 12). Knob 89 is configured to override the sloping surface of fins 200, but lodge firmly within the gap between the fins thereby retaining cover 60 in a selected position along body 24.

Preferably, protrusions 84 and/or knob 89 generate a clicking noise to confirm when they are engaged with the respective retention structures, thereby providing audible confirmation that the cover is properly located in the selected position.

Figure 10:
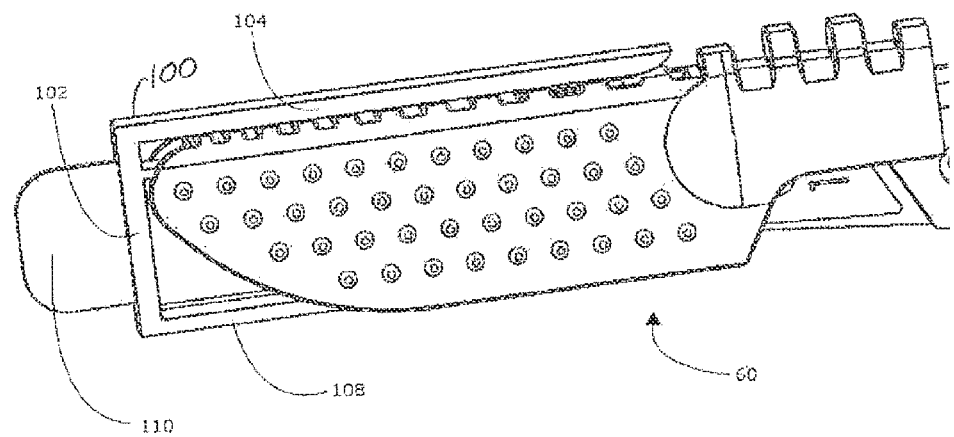
FIG. 10 is a side view of the blade unit with the removable safety guard.
Figure 11:
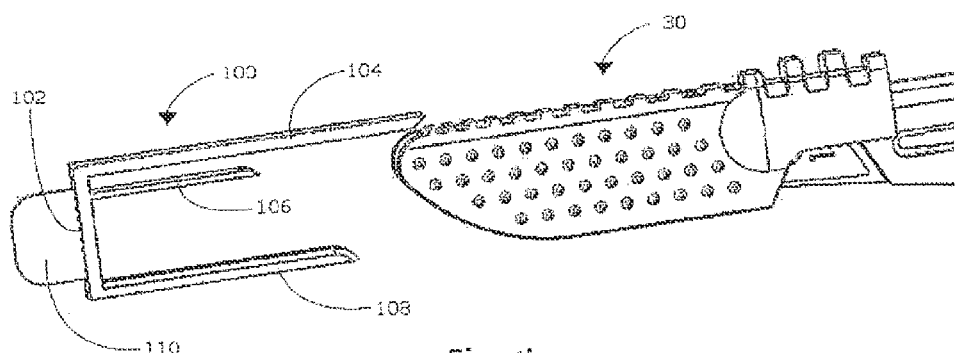
FIG. 11 is a side view of the blade unit, with the safety guard detached.

Referring to FIGS. 10 and 11, a removable guard 100 is provided. Guard 100 comprises a spine 102 and upper, middle and lower prongs 104, 106 and 108, which project rearwardly from spine 102. Guard 100 is configured such that upper and lower prongs frictionally engage the upper and lower surfaces of cover 60, and middle prong 106 slides into the space within cover 60 immediately below the upper surface thereof, above blade 15. When thus engaged, guard 100 is frictionally retained to cover 60 and prevents or reduces contamination of blade 15, and reduces the risk of contact with blade 15 with either a user or an external object. Removal of guard 100 is assisted by a forwardly-projection tab 110 which protrudes from spine 102.

Figure 18:
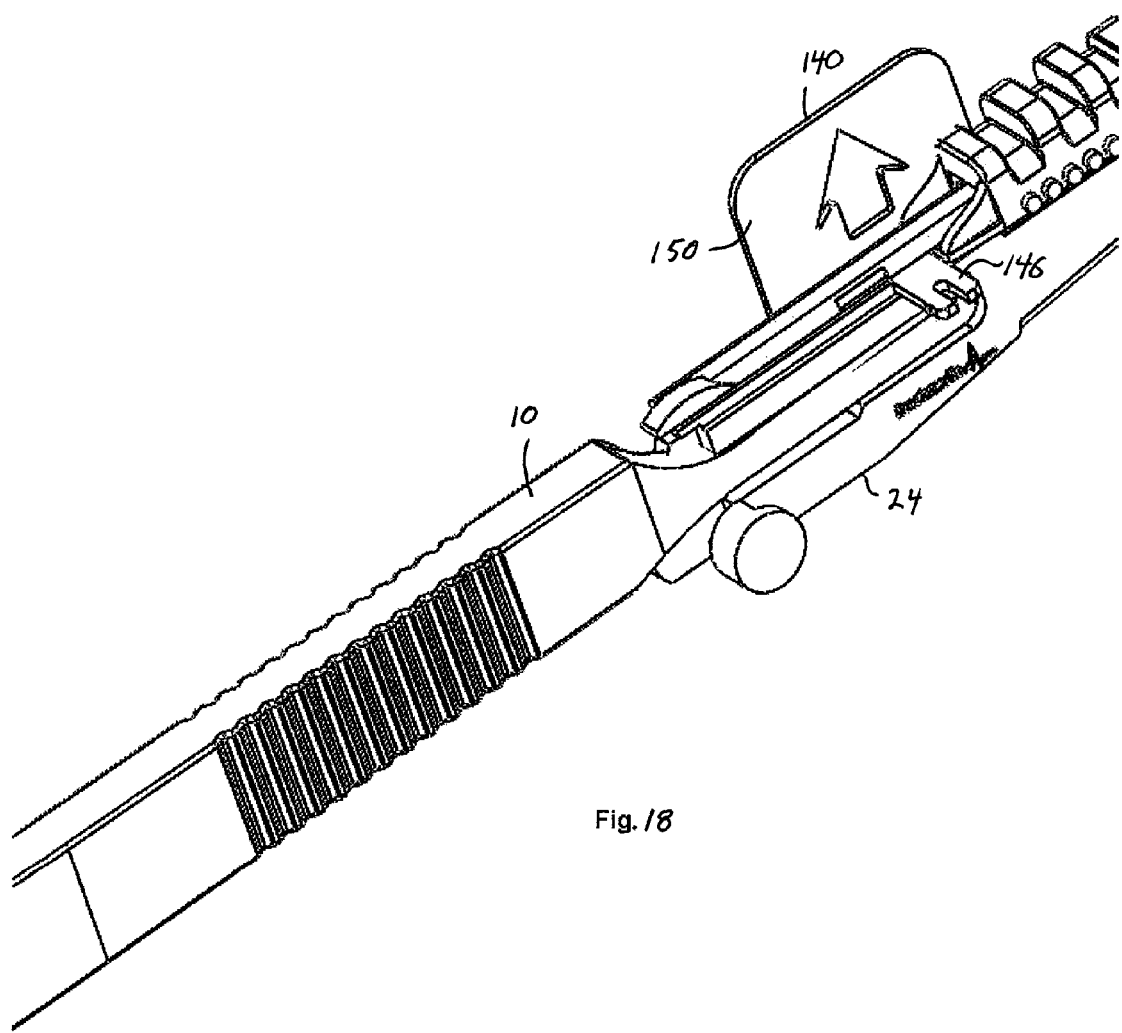
FIG. 18 is a perspective view of the second embodiment, showing an enlarged view of a portion thereof to illustrate the removable tab.
Figure 19:
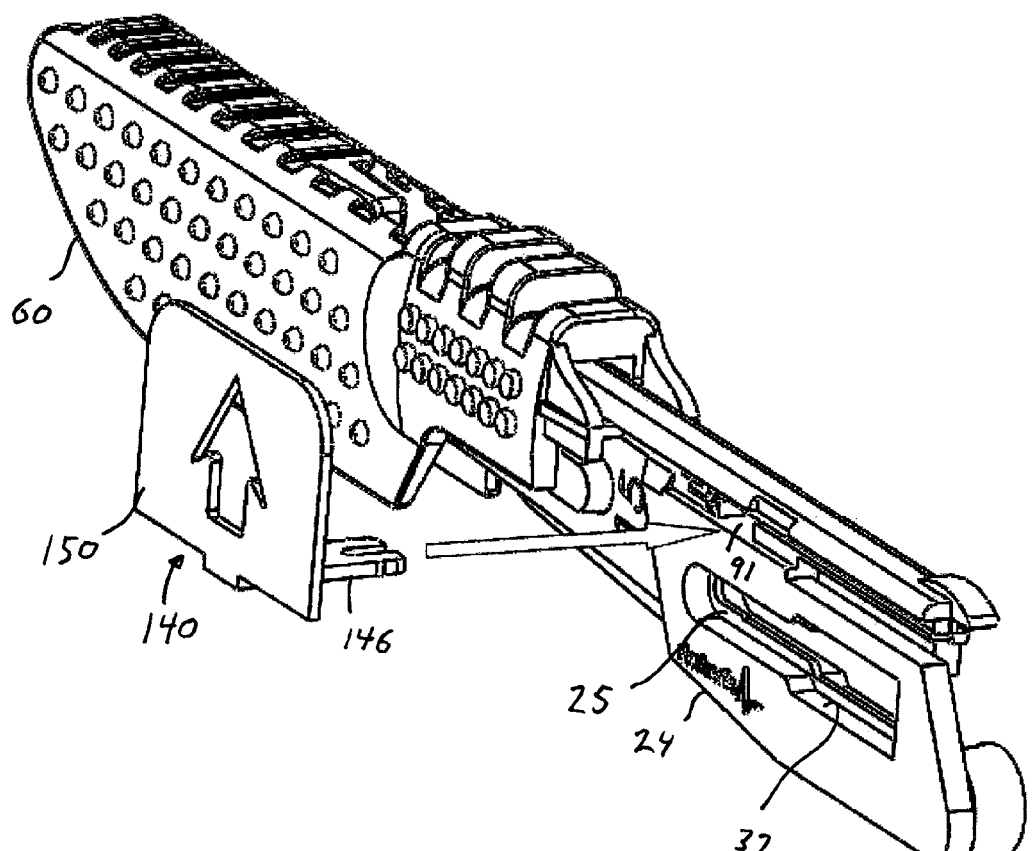
FIG. 19 is a perspective view as in FIG. 18, showing the tab removed from the body of the device.

FIGS. 18 and 19 illustrate a further embodiment, wherein the blade unit is provided with a removable locking tab 140.

Body 24 includes a transverse opening 91 (comprising the same opening 91 which serves to receive protrusions 84), in which opening 91 extends through wall 45. Tab 140 comprises a flat, upwardly-projecting finger grip portion 150, and a flat pin 146 projecting laterally from the base of finger grip portion 150. Opening 91 and pin 146 have a matching configuration (preferably rectangular) to permit pin 146 to fit snugly within opening 91 with sufficient frictional engagement to resist removal. Gripping portion 150 may include a cut-out shape such as an arrow, to indicate its orientation of insertion. Pin 146 has a length which is sufficient to fully traverse body 24, and to protrude laterally from the side opposed to portion 150. When fully inserted into body 24, pin 146 engages cover 60 to prevent retraction of the cover beyond the location of opening 91. Opening 91 is located at a position to retain cover 60 in its pre-use position when tab 140 is inserted therein, thereby prevented unwanted exposure of blade 15 until tab 140 is removed. Optionally, a second opening (not shown) is provided distally of the first opening, into which tab 140 may be inserted when the cover is placed in the disposal position, to assist in retaining the cover in this position. According to this version, gripping portion 150 may be snapped off along a perforation or weakened zone, to make it difficult to remove tab 140 once in the disposal mode.

It will be seen that blade unit described herein can be scaled up or down in size, and the configuration of the respective components thereof altered, to accommodate different sizes and configurations of blades. As well, different materials can be employed to serve various requirements, and other alterations may be made to the embodiments described herein.

A scalpel according to the present invention may be supplied to the user as a kit which includes a variety of blade units with a variety of blade sizes and types. Such a kit may include one or more handles, or alternatively may be provided in a form which relies on the user possessing a suitable handle. As an alternative to the intended use for surgical or other medical procedures, the invention may be intended for non-medical applications, such as woodworking or other hobbyist activities, or general purpose household uses, and blade 15 may comprise a blade suitable for such applications.

In one embodiment, not shown, the blade unit can be incorporated into a handle in a non-releasable fashion, wherein body 24 is incorporated into handle 10 in a permanent, non-releasable fashion. According to this aspect, sliding cover 60 is engaged to body 24 in a similar fashion as the embodiments described above. However, body 24 is either fixedly mounted to the handle in a non-releasable fashion or alternatively is incorporated with the handle to form a single unitary member therewith.

Although the present invention has been described in part by way of a detailed embodiment thereof, it will be seen by those skilled in the relevant art that the invention is not limited to the particular elements and aspects as described above. Rather, the invention includes numerous variations of and departures from this embodiment, including mechanical and functional equivalents of the elements described herein, as such equivalents would be reasonably understood by persons skilled in the art. The full scope of the present invention is defined by the present patent specification as a whole, including the claims, and including mechanical and functional equivalents of elements described herein.

What is claimed is:

1. A blade unit for releasable attachment to a scalpel handle wherein said handle comprises a hand grip and a finger projecting from said hand grip, said finger comprising opposing flat sides, upper and lower edges with blade-engaging grooves recessed into said upper and lower edges and a first boss projecting laterally from one of said flat sides configured for mounting a slotted scalpel blade to said handle; said blade unit comprising:
   a) the slotted scalpel blade having a first slot with a first configuration for mounting to a second boss;
   b) a blade support body made of a first rigid material, and comprising the second boss configured to receive the first slot of the slotted scalpel blade;
   c) a plate fixed within said blade support body, wherein the plate is made of a second rigid material, said plate comprising a second slot having a second configuration substantially identical to the first configuration wherein said second slot is configured to mount to the first boss of said handle and engage the blade-engaging grooves of the handle for releasably securing the blade support body to the handle via the plate; and
   d) a blade cover slideably engaged to said blade support body for movement between an extended position covering said blade and a retracted position to expose said blade for use.

2. The blade unit of claim 1 wherein the blade cover is engaged to the body by means of at least one mutually engaging channel and projection wherein said projection is configured to fit within said channel for sliding engagement between said channel and projection.

3. The blade unit of claim 2 wherein said body comprises at least two of said channels located in opposing sides of said body and said cover comprises opposing spaced apart flanks, said projections extending towards each other within the interior space between said flanks.

4. The blade unit of claim 2 wherein said channel is provided within said body and the projection extends from the cover, said body comprising a stop member to prevent the projection from traveling past the body in a proximal direction.

5. The blade unit of claim 1 wherein said blade unit is configured to selectively retain said cover in three positions, comprising a "pre-use" position wherein said cover fully covers said slotted scalpel blade for safe handling, a "retracted" position wherein the cover is retracted rearwardly to expose said slotted scalpel blade for use, and a "disposal" position wherein said cover is located forwardly past the "pre-use" position for removal of the blade unit from said handle for safe disposal, and wherein said cover is selectively mechanically retained in each of said positions by one or more mutually engaging retractable protrusions and detents of the blade unit.

6. The blade unit of claim 1 further comprising a guard configured for removable engagement to said cover to prevent said blade from protruding past said cover.

7. The blade unit of claim 1 wherein said blade cover comprises opposed spaced apart side walls and an upper wall between said side walls, said upper wall protruding from said side walls at a proximal end of said cover to form a contact surface for a user.

8. The blade unit of claim 1 wherein said cover is configured such that when in said retracted position, the sides of said handle are substantially exposed and uncovered by said cover.

9. The blade unit of claim 1 wherein said blade support body comprises windows on opposing sides thereof to expose the opposing sides of said plate.

10. The blade unit of claim 1 further comprising a removable tab for insertion in said body, said body having at least one transverse opening, wherein the tab comprises a pin for engagement within said opening to prevent retraction of said cover past said opening when engaged.

11. A scalpel or scalpel kit comprising:
i) a scalpel handle comprising a hand grip and a finger projecting from said hand grip, said finger comprising opposing flat sides, upper and lower edges with blade-engaging grooves recessed into said upper and lower edges and a first boss projecting laterally from one of said flat sides configured for mounting a blade to said handle; and
ii) a blade unit comprising:
 a) the blade having a first slot formed therein with a first configuration for mounting to a second boss;
 b) a blade support body made of a first rigid material and comprising the second boss configured to receive the first slot of the slotted scalpel blade
 c) a plate fixed within said blade support body, wherein the plate is made of a second rigid material, said plate comprising a second slot, having a second configuration substantially identical to the first configuration, the second slot configured to mount to the first boss of said scalpel handle and engage the blade-engaging grooves of the scalpel handle for releasable securing the blade support body to the scalpel handle via the plate;
 d) a blade cover slideably engaged to said blade support body; and
 e) one or more mutually engaging protrusions and detents, wherein said blade unit is configured to selectively mechanically retain said cover in each of three positions by the one or more mutually engaging protrusions and detents, wherein the three positions comprise a "pre-use" position wherein said cover fully covers said blade for safe handling, a "retracted" position wherein the cover is retracted rearwardly to expose said blade for use, and a "disposal" position wherein said cover is located forwardly past the "pre-use" position for removal of the blade unit from said handle for safe disposal for movement between an extended position covering said blade and a retracted position to expose said blade for use.

12. The scalpel or scalpel kit of claim 11 further comprising a removable tab for insertion in said body, said body having at least one transverse opening, wherein the tab comprises a pin for engagement within said opening to prevent retraction of said cover past said opening when engaged.

13. A blade unit for releasable attachment to a scalpel handle wherein said handle comprises a hand grip and a finger projecting from said hand grip, said finger comprising opposing flat sides, upper and lower edges with blade-engaging grooves recessed into said upper and lower edges and a first boss projecting laterally from one of said flat sides configured for mounting a blade to said handle, said blade unit comprising:
 a) the blade having a first slot configured for mounting to a second boss;
 b) a blade support body having a plastic portion comprising said second boss configured to receive the first slot for mounting the blade to the blade support body and a metal plate within said plastic portion for mounting the blade unit to the handle, the plate comprising a second slot substantially identical to the first slot, and configured to mount to the first boss and engage the blade-engaging grooves of the handle for releasably securing the blade support body to the handle; and
 c) a blade cover slideably engaged to said blade support body for movement between an extended position covering said blade and a retracted position to expose said blade for use.

14. The blade unit of claim 13 wherein the blade cover is engaged to the body by means of at least one mutually engaging channel and projection wherein said projection is configured to fit within said channel for sliding engagement between said channel and projection.

15. The blade unit of claim 14 wherein said body comprises at least two of said channels located in opposing sides of said body and said cover comprises opposing spaced apart flanks, said projections extending towards each other within the interior space between said flanks.

16. The blade unit of claim 14 wherein said channel is provided within said body and the projection extends from the cover, said body comprising a stop member to prevent the projection from traveling past the body in a proximal direction.

17. The blade unit of claim 13 wherein said blade unit is configured to selectively mechanically retain said cover in three positions, comprising a "pre-use" position wherein said cover fully covers said blade for safe handling, a "retracted" position wherein the cover is retracted rearwardly to expose said blade for use, and a "disposal" position wherein said cover is located forwardly past the "pre-use" position for removal of the blade unit from said handle for safe disposal.

18. The blade unit of claim 13 further comprising a guard configured for removable engagement to said cover to prevent said blade from protruding past said cover.

19. The blade unit of claim 18 wherein said guard comprises a removable tab for insertion in said cover, said cover having at least one laterally-oriented opening and said base having a recess aligned with said opening when in the retracted position, whereby insertion of said tab into said opening and recess substantially locks said cover to said base in the retracted position.

20. The blade unit of claim 13 wherein said blade cover comprises opposed spaced apart side walls and an upper wall between said side walls, said upper wall protruding from said side walls at a proximal end of said cover to form a contact surface for a user.

21. The blade unit of claim 13 wherein said cover is configured such that when in said retracted position, the sides of said handle are substantially exposed and uncovered by said cover.

22. The blade unit of claim 13 further comprising a removable tab for insertion in said body, said body having at least one transverse opening, wherein the tab comprises a pin for engagement within said opening to prevent retraction of said cover past said opening when engaged.

* * * * *